United States Patent [19]
Ravetta et al.

[11] Patent Number: 5,994,271
[45] Date of Patent: Nov. 30, 1999

[54] HERBICIDAL COMPOSITIONS, METHODS OF PREPARATION AND METHODS OF USE

[75] Inventors: Guido Ravetta, Milan; Giorgio Oberrauch, San Donato Milanese, both of Italy

[73] Assignee: I.Pi.Ci. S.p.A., Milan, Italy

[21] Appl. No.: 09/072,824

[22] Filed: May 5, 1998

[30] Foreign Application Priority Data

Jan. 20, 1998 [IT] Italy .................................. T098A0048

[51] Int. Cl.$^6$ .............................................. A01N 504/206
[52] U.S. Cl. ............................................................... 504/206
[58] Field of Search ................................. 71/86; 504/206

[56] References Cited

U.S. PATENT DOCUMENTS

| | | | |
|---|---|---|---|
| 908,493 | 10/1962 | Mackay et al. | 71/86 |
| 3,301,656 | 1/1967 | Campbell et al. | 71/28 |
| 3,458,303 | 7/1969 | Belak et al. | 71/64 |
| 3,853,530 | 12/1974 | Franz | 71/76 |
| 3,868,407 | 2/1975 | Franz et al. | 260/482 R |
| 3,888,915 | 6/1975 | Alt | 71/86 |
| 3,926,841 | 12/1975 | Habasko et al. | 252/383 |
| 3,948,975 | 4/1976 | Franz | 260/482 |
| 3,954,439 | 5/1976 | Papamichael et al. | 71/93 |
| 3,970,695 | 7/1976 | Rueppel | 260/534 |
| 3,971,648 | 7/1976 | Franz et al. | 71/86 |
| 3,979,200 | 9/1976 | Alt | 71/86 |
| 3,993,467 | 11/1976 | Franz | 71/86 |
| 4,035,176 | 7/1977 | Rueppel | 71/86 |
| 4,047,926 | 9/1977 | Rueppel | 71/86 |
| 4,047,927 | 9/1977 | Gaertner et al. | 71/86 |
| 4,062,669 | 12/1977 | Franz | 71/86 |
| 4,105,430 | 8/1978 | Koch et al. | 71/159 |
| 4,106,923 | 8/1978 | Franz | 71/86 |
| 4,120,689 | 10/1978 | Dutra | 71/93 |
| 4,130,412 | 12/1978 | Franz | 71/86 |
| 4,131,448 | 12/1978 | Franz | 71/86 |
| 4,140,513 | 2/1979 | Prill | 71/86 |
| 4,170,463 | 10/1979 | Large | 71/86 |
| 4,197,254 | 4/1980 | Gaertner | 260/502.5 |
| 4,289,525 | 9/1981 | Pasarela et al. | 71/92 |
| 4,336,052 | 6/1982 | Chen et al. | 71/28 |
| 4,356,020 | 10/1982 | Grünert et al. | 71/92 |
| 4,376,644 | 3/1983 | Large | 71/87 |
| 4,384,880 | 5/1983 | Large | 71/87 |
| 4,395,276 | 7/1983 | Sikorski et al. | 71/87 |
| 4,397,676 | 8/1983 | Bakel | 71/86 |
| 4,399,287 | 8/1983 | Baillie et al. | 548/119 |
| 4,407,764 | 10/1983 | Sikorski et al. | 260/940 |
| 4,414,158 | 11/1983 | Thummel et al. | 260/438.1 |
| 4,421,547 | 12/1983 | Prisbylla | 71/86 |
| 4,437,874 | 3/1984 | Large | 71/87 |
| 4,440,562 | 4/1984 | Prill | 71/86 |
| 4,444,581 | 5/1984 | Singh | 71/86 |
| 4,475,942 | 10/1984 | Bakel | 71/86 |
| 4,476,063 | 10/1984 | Felix | 260/940 |
| 4,483,705 | 11/1984 | Purdum | 71/86 |
| 4,486,356 | 12/1984 | Bakel | 260/501.12 |
| 4,505,736 | 3/1985 | Franz | 71/76 |
| 4,507,250 | 3/1985 | Bakel | 260/502.5 |
| 4,508,663 | 4/1985 | Sikorski et al. | 260/968 |
| 4,535,181 | 8/1985 | Felix | 560/172 |
| 4,545,804 | 10/1985 | Franz et al. | 71/86 |
| 4,554,009 | 11/1985 | Sikorski et al. | 71/87 |
| 4,634,788 | 1/1987 | Dhingra et al. | 558/145 |
| 4,735,649 | 4/1988 | Dhingra et al. | 71/86 |
| 5,118,338 | 6/1992 | Moller | 71/86 |

*Primary Examiner*—Jose' G. Dees
*Assistant Examiner*—Alton Pryor
*Attorney, Agent, or Firm*—Donald L. Rhoades; Todd J. Tiberi; Kramer Levin Naftalis & Frankel LLP

[57] ABSTRACT

The present invention relates to a herbicidal composition that is in the form of solid water dispersible granules (WDG) containing the compound N-phosphonomethylglycine (glyphosate acid) in an admixture with a surfactant that is comprised of one or more polyglycolethers, each having a waxy consistency, and each polyglycolether having a linear saturated alcohol having from about 10 to about 15 carbon atoms, which is ethoxylated with from about 30 to about 40 moles of ethylene oxide per mole of alcohol. This composition provides a combination of manufacturing and weed killing (i.e., herbicidal) advantages that heretofore have been unattainable with the use of either glyphosate acid or glyphosate in salt form. The present invention also relates to methods of using this composition and a process for preparing the WDG composition that comprises mixing the glyphosate acid with the surfactant and then extruding the mixture.

25 Claims, No Drawings

HERBICIDAL COMPOSITIONS, METHODS OF PREPARATION AND METHODS OF USE

BACKGROUND OF THE INVENTION

The present invention relates to a novel herbicidal composition in the form of solid water dispersible granules (WDG) containing the compound N-phosphonomethylglycine (glyphosate acid) in an admixture with a particular non-ionic surfactant. This composition provides a combination of manufacturing and weed killing (i.e., herbicidal) advantages that heretofore have been unattainable with the use of either glyphosate acid or glyphosate in salt form. The present invention also relates to a novel process for preparing this novel WDG composition.

Glyphosate in the form of its salts, as opposed to glyphosate in its acid form, is the most common form of glyphosate that is used as an active agent in agriculture and industrial herbicidal liquid formulations (soluble liquids) or solid formulations (soluble powders or water dispersible). Glyphosate acid has the following structure:

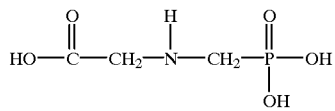

Glyphosate salts have been preferred because of glyphosate acid's relative lack of solubility in water and other solvents that are commonly used both to process glyphosate and to apply glyphosate in herbicidal applications. Thus, glyphosate salts have been chosen as the form to use in the vast majority of herbicidal applications because, before this invention, they were easier to use both when manufacturing the herbicidal formulations and when the end user makes the final herbicidal formulation that was applied to weeds and other undesired plants.

The glyphosate salt compositions are generally used in liquid formulations composed of glyphosate itself in the amount of from 2% to 40% by weight in a salt form and a suitable coadjuvant (i.e., surfactant) which enhances the absorption of the active agent in the undesired plants. The salt forms commonly contain glyphosate with amines or other cations. The amines and cations include isopropylamine in the case of liquid formulations (soluble liquids) and ammonium or sodium salts for solid type formulations such as WDG. The past work of others has largely focused on solving problems associated with making the glyphosate salt compounds easier to process and then apply as herbicides. These problems with using glyphosate salts include their hygroscopic nature which can lead to processing (e.g., clogging) and storage (e.g., deliquescence) problems.

The reported attempts to use glyphosate acid instead of the salt forms of glyphosate to avoid the aforementioned problems associated with using the salt forms have not been capable of producing a composition with the advantages of the present invention. These reported compositions have substantial disadvantages which include disadvantages in the manufacturing of the herbicidal composition, requiring the use of unfavorable processing conditions, or the addition of extra ingredients such as acid acceptors and extrusion aids. Other disadvantages arise in the final use of the composition to kill undesired plants.

Specifically, U.S. Pat. No. 5,118,338 described a water soluble herbicidal formulation in the form of powder or granules which can include glyphosate acid and a non-ionic surfactant. This surfactant consists of a polyglycolether of a fatty alcohol having from 16 to 18 carbon atoms which is ethoxlyated with about 25 units of ethylene oxide per mole of fatty alcohol. The surfactant that was chosen is itself in a granular or powdery form and the disclosure explicitly excludes the use of waxy surfactants. This formulation does not allow the preparation of granules by direct extrusion in the absence of further extrusion aids.

EP-A-0 582 561 describes a herbicidal formulation containing glyphosate in admixture with a surfactant which is preferably liquid at ambient temperature with an extrusion aid added consisting of a polyalkyleneglycol. All of the formulations which are specifically disclosed in the working examples relate to glyphosate in a salt form with an alkali metal or ammonium. The use of an extrusion aid is described as essential in order to obtain anhydrous formulations in granular form by the extrusion process.

WO 92/12637 describes anhydrous formulations of glyphosate containing an acid acceptor and optionally a surfactant. Thus, this formulation requires the addition of an extra ingredient, the acid acceptor, in order to make the composition processable and useable as a herbicide.

In light of these problems, it would be desirable to provide herbicidal compositions and formulations containing glyphosate acid that do not have the substantial disadvantages of the compositions and formulations of the past.

SUMMARY OF THE INVENTION

With these problems and disadvantages from prior compositions and formulations in mind, a number of objectives of the present invention were sought and obtained. One such objective of the present invention is to provide a composition and herbicidal formulation based on glyphosate acid in granular form with a surfactant which does not form chemical bonds with the glyphosate acid itself, either during the manufacturing steps or during the preparation of the dilute solution of the composition of glyphosate acid and surfactant in water, which is carried out just prior to spraying on weeds. Another objective of the invention is to make a composition and formulation which is free from further coadjuvants such as wetting agents or extrusion aids but which is still relatively easy to process and use.

Another objective of the invention is to provide a formulation containing the glyphosate acid which has herbicidal properties which are comparable or better than the presently used formulations which contain glyphosate acid or glyphosate in salt form. Thus, a formulation that has comparable activity to another formulation but which has other more favorable characteristics such as better processability or storage characteristics, is highly desirable. Another objective of the invention is that the formulations have a broad or even broader spectrum of weed and other plant control than the formulations used before.

A further objective of the invention is to provide a formulation which maintains or improves the penetrability and therefore the activity rate of the active agent, glyphosate, with respect to the formulations used before.

Still another objective of the invention is to provide a formulation which is suitable to maintain or even increase the concentration of glyphosate in the formulation itself, since a reduced content of inert material reduces the transportation costs, improves the handling of the packaging, and reduces the amounts of chemical products which are introduced into the environment.

Still another objective of the invention is to provide a formulation which is stable against freezing due to its structure and composition.

Still another objective of the invention is to provide a formulation which may be obtained by means of currently used industrial machinery and to also obtain formulations which are stable for a long period of time.

Various studies have been done by the present inventors to solve the problems associated with the use of glyphosate acid in herbicidal formulations and to obtain a number of goals, including without limitation the objectives set forth above. As a result of these studies, the present inventors have discovered a composition that solves the problems and disadvantages of compositions used in the past. The invention, which is also described further herein, is a composition comprising glyphosate acid and a particular non-ionic surfactant. The surfactant is comprised of one or more polyglycolethers, each having a waxy consistency, and each polyglycolether having a linear saturated alcohol having from about 10 to about 15 carbon atoms, which is ethoxylated with from about 30 to about 40 moles of ethylene oxide per mole of alcohol.

The present inventors also discovered a preferred method of preparing or manufacturing this novel composition by mixing the glyphosate acid and surfactant and then extruding the resulting mixture. Such a process can be accomplished by the following steps:

a. charging the glyphosate acid, preferably in crystalline form, into a mixer, b. melting the surfactant, c. spraying the molten surfactant onto the glyphosate acid in the mixer, d. adding a concentration of water to the mixer that is between about 3% and about 15% by weight of the entire formulation (preferably from about 5% to about 10% by weight) without dissolving an appreciable amount of glyphosate acid or the surfactant, e. feeding the resulting mixture into a low pressure extruder, f. forcing the mixture through holes of an extrusion die having a diameter from about 0.3 to about 1.2 mm (preferably from about 0.4 to about 0.8 mm), g. separating the extrusion into granules (preferably having a length of about 2 to about 3 mm), h. drying the granules in a continuous air drier at low atmospheric pressure and temperature (preferably not higher than about 60° C.).

Of course, the extrusion can also be processed into forms other than granules such as pellets, flakes, powders or other forms that are known to those skilled in the art.

The resulting composition from this process has a unique combination of advantages in terms of processability, useability and convenience that have substantial commercial benefits.

DETAILED DESCRIPTION OF THE INVENTION

The glyphosate acid used in this invention is N-phosphonomethylglycine. Different forms of glyphosate acid can be used, although the crystalline powder is preferred. The formulation preferably comprises from about 40% to about 90% by weight of glyphosate acid and correspondingly from about 60% to about 10% by weight of the surfactant.

A particular non-ionic surfactant is used in this invention. This surfactant is comprised of one or more polyglycolethers, each having a waxy consistency, and each polyglycolether having a linear saturated alcohol having from about 10 to about 15 carbon atoms, which is ethoxylated with from about 30 to about 40 moles of ethylene oxide per mole of alcohol. Preferably, the surfactant is a mixture of natural or synthetic alcohols having a straight saturated chain with from about 12 to about 15 carbon atoms, which are ethoxylated with from about 30 to about 40 moles of ethylene oxide. These surfactants are available on the market (see Example 1 for one such surfactant) or they can be obtained by known ethoxylation processes from saturated linear alcohols. In a preferred embodiment, the surfactant has an HLB value higher than about 17.

According to the previous disclosures of certain others, the possibility of using non-ionic surfactants of a waxy consistency was explicitly excluded. However, it has been surprisingly found that these non-ionic surfactants defined in the paragraph above, with their waxy consistency, make it possible to obtain compositions and formulations which are easily extruded without the need of adding extrusion aids and which make it possible to obtain a granular water soluble product which fulfills the above mentioned objectives of the invention. The surfactant preferably has this waxy consistency at ambient temperature.

The composition of this invention can be dissolved in water and applied by conventional means to undesirable plants, preferably by spray, at usual rates of application. Effective plant elimination and control is achieved. Well-known additives also can be added to this solution of the disclosed composition mixed with water, with or without the need for other penetrating agents, such as wetting agents. Furthermore, the composition of this invention can be used in combination with other active ingredients, such as Sulfometuron, Metsulfuron, Diuron, Bromacil, etc, according to their tank mixing procedures. In this way, the composition, when appropriately mixed with water and otherwise prepared as described herein, can be used to prepare a formulation that is useful as a herbicide to control undesired plants such as weeds. Selective killing of undesired plants such as weeds can also be accomplished by application of the appropriately prepared formulation if the undesired plants are growing with desired plants (such as crops) which are resistant to glyphosate acid.

The herbicidal formulation of this invention is preferably obtained by an extrusion process after mixing the glyphosate acid and surfactant. The preferred preparation process comprises a first mixing stage, wherein glyphosate acid, preferably as a crystalline powder, is first charged into a mixer. Concurrently, the surfactant which is described above, having a waxy consistency at ambient temperature, is heated to a temperature higher than about 50° C. or to a temperature necessary to melt it. The surfactant is then sprayed on the bulk of glyphosate acid under stirring conditions. Preferably, the molton surfactant hardens in the air as it is sprayed, and thus forms solid particles of a relatively uniform size before it contacts the glyphosate acid. At the end of this stirring, an amount of water (preferably between about 3% and about 15%, most preferably between about 5% and about 10% by weight) is added. The thus obtained mixture has highly favorable processing characteristics. It does not clog the necessary machinery and it has exceptional handling characteristics. It is then fed to an extruder operating at relatively low pressure and extruded through an extrusion die having holes with a diameter from about 0.3 to about 1.2 mm, preferably of from about 0.4 to about 0.8 mm. The thus obtained extrusion is cut into granules having a preferable length of from about 2 to about 3 mm. The granules are than charged into a continuous air drier and are dried at a relatively low temperature, preferably not higher than about 60° C.

The extrusion can also be processed into forms other than granules such as pellets, flakes, powders or other forms that are known to those skilled in the art.

These granules or other forms can be appropriately packaged and, when needed, be added to water as described above to produce a solution that is useful as a herbicide.

Thus it has been found that by following the teachings described herein, a highly effective glyphosate acid containing composition and herbicidal formulation may be obtained. In this composition, chemical bonds between the surfactant and glyphosate acid may be avoided. The final formulation may be successfully processed and applied as a spray without the need for further adjuvants such as wetting agents, extrusion aids and acid acceptors, thus saving costs and reducing the amounts of chemical products introduced into the environment.

Furthermore, by following the teachings described herein a highly concentrated glyphosate acid formulation can be obtained which may decrease transportation and handling costs associated with the product. For example, formulations containing glyphosate in its salt form are often packaged with 50% by weight or more of water. If the formulation of this invention is packaged and shipped in a dry form such as WDG, without water, the product's weight will be dramatically less. Another advantage is if this dry form is spilled by accident, it is easier to clean-up, presenting less of an environmental risk.

The formulation produced is highly stable and resistant to decomposition in low temperatures. The formulation also is resistant to accumulating water and is a highly active herbicide with a wide-range of activity.

Example 1 is an illustration of a method that may be used to prepare the claimed composition. Example 2 is an illus-

EXAMPLE 1

1.66 kg of technical grade glyphosate acid in the form of a crystalline powder were fed to a Lodige type mixer. After having started the mixer, 0.34 kg of the surfactant, Rhodasurf M/30™ from Rhone-Poulenc, which had been brought to the molten state at 40–50° C., were sprayed onto the acid glyphosate. After having mixed the bulk for 5 minutes, the bulk was sprayed with 0.15 kg water.

The mixer was allowed to run for 5 additional minutes, after the end of the water spray.

Then, the mixture of glyphosate acid, surfactant and water was transferred to the feeding device of a Fuji Paudal extruder, having an extrusion die with holes having a diameter of 0.4 mm. The extruder was run at a low pressure and granules were obtained having a length of 2–4 mm and a diameter of about 0.4 mm. The granules were then dried in an air stream at 60° C.

EXAMPLE 2

The herbicidal activity of the novel glyphosate acid/surfactant formulation as described in Example 1 was compared to two commercially available products.

To prepare the formulation of Example 1 for application on the weeds, the described granules were dissolved in water and 0.5% by weight of the adjuvant RNA was added. This solution and the comparison products (made according to their packaging instructions) were applied to the weeds by conventional spraying at a rate indicated below. Fourteen days after the application, the effectiveness was evaluated as percentage of the killed weeds. The results are given in the following table:

|  | Rate | % Kill | | | | | | | | |
|---|---|---|---|---|---|---|---|---|---|---|
|  |  | Chenopodium album | Lamium amplaxicaule | Ameinckia Intermedia | Convolvulus arvensis | Cynodon dactylon | Maiva parviflora | Taraxacum officinate Wiggers | Digitaris lachaemum | Digitaria senguina |
| Product from Ex. 1 | 0.9 lb/A (a) | 100.0 | 87.5 | 100.0 | 100.0 | 83.8 | 100.0 | 93.6 | 100.0 | 100.0 |
| Product from Product Ex. 1 | 0.72 lb/A (b) | 100.0 | 80.0 | 100.0 | 100.0 | 86.3 | 100.0 | 98.8 | 100.0 | 100.0 |
| Roundup Ultra | 32 oz/A (c) | 100.0 | 90.0 | 100.0 | 98.8 | 86.3 | 100.0 | 98.8 | 100.0 | 100.0 |
| Roundup Ultra | 25.6 oz/A (d) | 100.0 | 88.8 | 100.0 | 100.0 | 83.8 | 100.0 | 100.0 | 100.0 | 100.0 |
| Untreated |  | 0.0 | 0.0 | 0.0 | 0.0 | 0.0 | 0.0 | 0.0 | 0.0 | 0.0 |

(a): 0.1 g/m$^2$ corresponding to 0.08 g glyphosate acid 100%/m$^2$
(b): 0.08 g/m$^2$ corresponding to 0.065 g glyphosate acid 100%/m$^2$
(c): 0.22 g/m$^2$ corresponding to 0.08 g glyphosate acid 100%/m$^2$
(d): 0.18 g/m$^2$ corresponding to 0.065 g glyphosate acid 100%/m$^2$ tration of a method used to evaluate the herbicidal activity of the composition disclosed herein in comparison with two products currently available on the market. These illustrative examples as well as the embodiments described above are not meant to be limiting, as it is apparent to one of skill in the art that one can use various equivalents, changes and modifications and still be within the scope of the present invention. Furthermore, the use of the words "composition" and "formulation" as used herein are not meant to be limiting and their meanings as they are used herein are interchangeable.

We therefore claim our invention as follows:

1. A composition of matter comprising glyphosate acid in admixture with a non-ionic surfactant, said surfactant comprising one or more polyglycolethers, each having a waxy consistency, and each polyglycolether comprising a linear saturated alcohol having from 10 to 15 carbon atoms, which is ethoxylated with from 30 to about 40 moles ethylene oxide per mole of alcohol.

2. The composition of matter of claim 1 wherein the alcohol of the polyglycolether is a straight saturated chain with from about 12 to 15 carbon atoms.

3. The composition of matter of claim 1 wherein the polyglycolether has an HLB of greater than or equal to about 17.

4. The composition of matter of claim 1 which is comprised of about 40% to about 90% glyphosate acid and about 60% to about 10% surfactant.

5. A method of preparing the composition of matter of claim 1 comprising mixing the glyphosate acid and surfactant and extruding the resulting mixture.

6. A method of preparing the composition of matter of claim 1 comprising:
   a. charging the glyphosate acid into a mixer,
   b. melting the surfactant,
   c. spraying the molten surfactant onto the glyphosate acid that is in the mixer,
   d. adding a concentration of water to the mixer that is between about 3% and 15% by weight of the entire composition,
   e. feeding the resulting mixture into an extruder,
   f. forcing the mixture through holes of an extrusion die having a diameter from about 0.3 to about 1.2 mm, and
   g. drying the extruded mixture.

7. A method of killing or controlling undesired plants and weeds comprising mixing a herbicidally effective amount of the composition of matter of claim 1 with a solution comprising water and applying the resulting solution onto the undesired plants.

8. A method of selectively killing or controlling undesired plants and weeds while not injuring desired plants such as crops which are resistant to glyphosate acid, comprising mixing a herbicidally effective amount of the composition of matter of claim 1 with a solution comprising water and applying the resulting solution onto the undesired plants and the desired plants.

9. A product comprising the composition of matter of claim 1 prepared by the process comprising mixing the glyphosate acid and surfactant and extruding the resulting mixture.

10. A product comprising the composition of matter of claim 1 prepared by the process comprising:
    a. charging the glyphosate acid into a mixer,
    b. melting the surfactant,
    c. spraying the molten surfactant onto the glyphosate acid that is in the mixer,
    d. adding a concentration of water to the mixer that is between about 3% and 15% by weight of the entire composition,
    e. feeding the resulting mixture into an extruder,
    f. forcing the mixture through holes of an extrusion die having a diameter from about 0.3 to about 1.2 mm, and
    g. drying the extruded mixture.

11. A herbicidal formulation comprising the composition of matter of claim 1 mixed with water.

12. A method of preparing the herbicidal formulation of claim 11 comprising mixing the glyphosate acid and surfactant, extruding the resulting mixture and adding water to the extruded mixture.

13. A method of preparing the herbicidal formulation of claim 11 comprising:
    a. charging the glyphosate acid into a mixer,
    b. melting the surfactant,
    c. spraying the molten surfactant onto the glyphosate acid that is in the mixer,
    d. adding a concentration of water to the mixer that is between about 3% and 15% by weight of the entire composition,
    e. feeding the resulting mixture into an extruder,
    f. forcing the mixture through holes of an extrusion die having a diameter from about 0.3 to about 1.2 mm,
    g. drying the extruded mixture, and
    h. adding water to the dried extruded mixture.

14. A method of killing or controlling undesired plants and weeds comprising applying the herbicidal formulation of claim 11 onto the undesired plants.

15. A method of selectively killing or controlling undesired plants and weeds while not injuring desired plants such as crops which are resistant to glyphosate acid, comprising applying the herbicidal formulation of claim 11 onto the undesired plants and the desired plants.

16. A product comprising the herbicidal formulation of claim 11 prepared by the process comprising mixing the glyphosate acid and surfactant, extruding the resulting mixture and adding water.

17. Water dispersible granules comprising the composition of matter of claim 1 in the form of water dispersible granules.

18. A method of preparing the water dispersible granules of claim 17 comprising mixing the glyphosate acid and surfactant, extruding the resulting mixture, and granulating the extruded mixture.

19. A method of preparing the water dispersible granules of claim 17 comprising:
    a. charging the glyphosate acid into a mixer,
    b. melting the surfactant,
    c. spraying the molten surfactant onto the glyphosate acid that is in the mixer,
    d. adding a concentration of water to the mixer that is between about 3% and 15% by weight of the entire composition,
    e. feeding the resulting mixture into an extruder,
    f. forcing the mixture through holes of an extrusion die having a diameter from about 0.3 to about 1.2 mm,
    g. separating the extrusion into granules, and
    h. drying the granules.

20. The method of claim 19 wherein the concentration of water that is added in d. is between about 5% to about 10% by weight of the entire composition.

21. The method of claim 19 wherein the holes of the extrusion die have a diameter from about 0.4 to about 0.8 mm.

22. The method of claim 19 wherein the water dispersible granules are made into lengths of about 2 to about 3 mm.

23. The method of claim 19 wherein the water dispersible granules are dried in a continuous air drier at low atmospheric pressure and at a temperature not higher than about 60° C.

24. A method of killing or controlling undesired plants and weeds comprising mixing a herbicidally effective concentration of the water dispersible granules of claim 19 with a solution comprising water and applying the resulting solution onto the undesired plants.

25. A method of selectively killing or controlling undesired plants and weeds while not injuring desired plants such as crops which are resistant to glyphosate acid, comprising mixing a herbicidally effective concentration of the water dispersible granules of claim 19 with a solution comprising water and applying the resulting solution onto the undesired plants and the desired plants.

* * * * *